United States Patent
Winkel et al.

(10) Patent No.: US 6,247,738 B1
(45) Date of Patent: *Jun. 19, 2001

(54) ROBOT HAND (75) Inventors: Axel Winkel, Zapel Hof; Patrick Scherr, Schwerin, both of (DE)

(73) Assignee: Daum GmbH, Schwerin (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/009,059

(22) Filed: Jan. 20, 1998

(51) Int. Cl.$^7$ .................................................. B25J 15/10
(52) U.S. Cl. ................................. 294/111; 414/7; 901/36; 901/39
(58) Field of Search .................. 294/106, 111, 294/902; 414/1–7; 901/31–34, 36–39; 623/63–65

(56) References Cited

U.S. PATENT DOCUMENTS

| | | |
|---|---|---|
| 422,373 | 3/1890 | Caldwell . |
| 2,435,614 * | 2/1948 | Tureman, Jr. ......................... 623/63 |
| 2,733,545 | 2/1956 | Guadagna . |
| 2,765,930 | 10/1956 | Greer et al. . |
| 3,212,651 | 10/1965 | Specht et al. . |
| 3,266,059 | 8/1966 | Stelle . |
| 4,298,300 | 11/1981 | Francois et al. . |
| 4,302,138 | 11/1981 | Zarudiansky . |
| 4,315,650 | 2/1982 | Yoshida . |
| 4,575,297 | 3/1986 | Richter . |
| 4,792,173 | 12/1988 | Wilson . |
| 4,834,761 | 5/1989 | Walters . |
| 4,921,293 | 5/1990 | Ruoff et al. . |
| 4,957,320 * | 9/1990 | Ulrich ................................. 294/111 |
| 4,986,723 | 1/1991 | Maeda . |
| 5,062,673 * | 11/1991 | Mimura ............................... 294/111 |
| 5,092,646 | 3/1992 | Smallridge . |
| 5,143,505 * | 9/1992 | Burdea et al. ......................... 414/5 |
| 5,447,403 | 9/1995 | Engler, Jr. . |
| 5,502,363 | 3/1996 | Tasch et al. . |
| 5,570,920 * | 11/1996 | Crisman et al. ..................... 294/111 |
| 5,599,151 * | 2/1997 | Daum et al. ........................ 294/111 |
| 5,776,126 * | 7/1998 | Wilk et al. .............................. 414/1 |
| 5,792,135 | 8/1998 | Madhani et al. . |
| 5,797,900 | 8/1998 | Madhani et al. . |
| 5,807,377 | 9/1998 | Madhani et al. . |
| 5,976,122 | 11/1999 | Madhani et al. . |

FOREIGN PATENT DOCUMENTS

| | | |
|---|---|---|
| 335838 | 4/1921 | (DE) . |
| 2 048 563 | 5/1980 | (DE) . |
| 2 939 452 | 2/1983 | (DE) . |
| 225 619 A1 | 4/1985 | (DE) . |

(List continued on next page.)

OTHER PUBLICATIONS

Proceedings 1990 IEEE International Conference on Robotics and Automation, May 13–19, 1990, IEEE Computer Society Fukuda et al.: "Distributed Type of Actuators by Shape Memory Alloy and its Application to Underwater Mobile Robotic Mechanism" pp. 1316–1321.

Gliederung von Manipulaturen, Die Technik, Feb. 2, 1964, pp. 92–96.

*Primary Examiner*—Dean J. Kramer
(74) *Attorney, Agent, or Firm*—Altera Law Group, LLC (57) ABSTRACT

The invention provides a robot hand that can mimic the movements of a human hand in operation. The robot hand includes a thumb and at least one opposing finger having at least two phalanxes connectable to each other by a distal phalanx joint. The thumb of the robot hand also includes a joint which allows the thumb to move transversely with respect to the opposing fingers. The robot hand can also include one or more additional fingers disposed on an opposite side of the thumb. The robot hand can be operated mechanically or electrically through controlling motors.

40 Claims, 7 Drawing Sheets

FOREIGN PATENT DOCUMENTS

| | | |
|---|---|---|
| 42 23 792 C1 | 9/1993 | (DE) . |
| 43 06 786 | 2/1994 | (DE) . |
| 0 640 319 B1 | 3/1995 | (EP) . |
| 0 688 538 A1 | 12/1995 | (EP) . |
| 2 013 617 | 8/1979 | (GB) . |
| 2 416 094 | 8/1979 | (FR) . |

* cited by examiner

ROBOT HAND

The U.S. Government has a nonexclusive, nontransferable, irrevocable paid-up license to practice or have practiced this invention for or on its behalf as provided for by the terms of Grant Number DAMD17-94-J-4502 awarded by the U.S. Department of the Army.

FIELD OF THE INVENTION

The invention is directed to a controllable remote grasping device, more particularly, a robot hand, which can be used in a remote manipulator, such as a surgical manipulator as described in U.S. patent application, Ser. No. 08/206,450, filed Mar. 4, 1994, now issued as U.S. Pat. No. 5,599,151, which is hereby incorporated by reference, and the like use.

BACKGROUND OF THE INVENTION

Manipulable hand apparatuses have been disclosed and are available in many industries, e.g. the medical device industry. The following references disclose examples of different types of manipulable hand apparatuses or handling devices used in the medical or other industries: U.S. Pat. No. 4,315,650 issued to Yoshida; U.S. Pat. No. 4,575,297 issued to Richter; U.S. Pat. No. 2,733,545 issued to Guadagna; U.S. Pat. No. 422,373 issued to Caldwell; U.S. Pat. No. 2,765,930 issued to Greer et al.; U.S. Pat. No. 3,212,651 issued to Specht et al; and European Patent Application Publication No. 0 640 319 A1 to Ortiz. In these references, different mechanical structures are utilized to control movements of a hand-type clamping device which is remotely controlled by a master control such as a human's hand, etc. However, most of these conventional clamping devices are complicated in structure. In addition, the conventional devices do not permit performance as a virtual hand at a remote site under master control. As a result, the conventional devices do not provide for a surgeon to perform surgery through a virtual reality modality. Further, even if the conventional devices are substantially altered to function as a virtual hand by adding numerous other pieces, the devices are too expensive to make and not practical in use.

Therefore, a substantial need exists for a robot hand which provides for an easy mechanism and is capable of performing surgery by transmission of the movement of a surgeon's hand.

SUMMARY OF THE INVENTION

The invention is directed to a controllable remote grasping device, more particularly, a robot hand, which can be used as a remote manipulator, such as a surgical manipulator, and the like use.

In one embodiment generally in accordance with the principles of the present invention, a robot hand comprises a thumb including at least two phalanxes connectable to each other by a first thumb joint and having a second thumb joint which allows the thumb to move transversely with respect to the phalanxes; at least two fingers, disposed on an opposite side of the thumb, each including at least two phalanxes connectable to each other by a first finger joint; the thumb being movable such as to oppose a selected one of at least two fingers and is able to individually grip between the selected finger and the thumb.

In some embodiments, at least one cable is connected to at least one of the phalanxes of each of the fingers and the thumb to move the phalanxes of each of the fingers and the thumb relative to each other. The cable can be operated from the proximal aspect of the robot hand by a controller.

The phalanxes of the robot hand are rotatable relative to one another to selectively cause the phalanxes to assume a bent or linear position by pushing or pulling on the cable. The phalanxes can be spring-biased to move from the bent position into a straight position by a spiral spring. The cable can pass through the spiral spring. In an alternative embodiment, the phalanxes are spring-biased to move from the bent position into a straight position by a flat spring. When all the fingers and thumb are in a substantially linear position, a robot hand of a suitable size can be passed through a medical trocar or the like. This advantageously provides for a robot hand of the invention to be used during minimally invasive surgical procedures, for example, a laparoscopic procedure.

A disposable glove can be applied over the robot hand to cover the thumb and the fingers for uses such as during endoscopic surgery. The glove is removed and renewed after a surgical operation.

In some embodiments, the robot hand can be operated remotely by a controlling system and the robot hand can be disconnected and removed from the controlling system for sterilization, maintenance, etc.

The remote grasping device can also comprise: a hand base; a first digit member, the first digit member including: a first distal phalanx, a first middle phalanx, and a first base phalanx, wherein the first base phalanx is pivotally attached to the hand base and constructed and arranged to provide for the first distal phalanx and the first middle phalanx to rotate as a single unit in at least two planes. A second digit member is arranged opposite of the first digit member, the second digit member including: a second distal phalanx, a second middle phalanx, and a second base phalanx, wherein the second base phalanx is pivotally attached to the hand base and constructed and arranged to provide for the second distal phalanx and the second middle phalanx to rotate as a single unit in at least two planes.

The movements of the first and second digit members can be mechanically or electrically controlled. In one embodiment, the movements of the first and second digit members can be controlled by a data glove.

In a further embodiment of the remote grasping device, the first distal phalanx can have a proximal end; the first middle phalanx can have a proximal end and a distal end and the first base phalanx can have a distal end. The proximal end of the first distal phalanx is pivotably attached to the distal end of the first middle phalanx for rotation around a first distal axis, and the proximal end of the first middle phalanx is pivotably attached to the distal end of the first base phalanx for rotation around a first middle axis. The first proximal axis and the first middle axis are substantially parallel provided that the first middle phalanx is generally linear. In addition, the second distal phalanx can have a proximal end and the second middle phalanx can have a proximal end and a distal end. The second base phalanx can have a distal end. The proximal end of the second distal phalanx is pivotably attached to the distal end of the second middle phalanx for rotation around a second distal axis, and the proximal end of the second middle phalanx is pivotably attached to the distal end of the second base phalanx for rotation around a second middle axis. The second proximal axis and the second distal axis are substantially parallel provided that the first middle phalanx is generally linear.

One advantage of the present invention is that it provides an easy mechanism for a robot hand. Another advantage of the invention is that it allows the use of right and left robot hands together at a surgical site which can work collectively like a human surgeon's hands. Such a system would provide for a surgeon to perform surgery through a virtual reality modality. Such a system would also permit skilled or specialized surgeons from one location to perform surgery at another location by transmission of surgeon's right and left hand movements to the right and left hand movements of robot's hands.

These and other advantages and features, which characterize the invention are pointed out with particularity in the claims annexed hereto and forming a part hereof. However, for a better understanding of the invention and the advantages and objectives obtained by its use, reference should be made to the drawings which form a further part hereof and to the accompanying descriptive matter, in which there is described a preferred embodiment of the invention.

DETAILED DESCRIPTION OF THE PREFERRED EMBODIMENT

Figure 1:
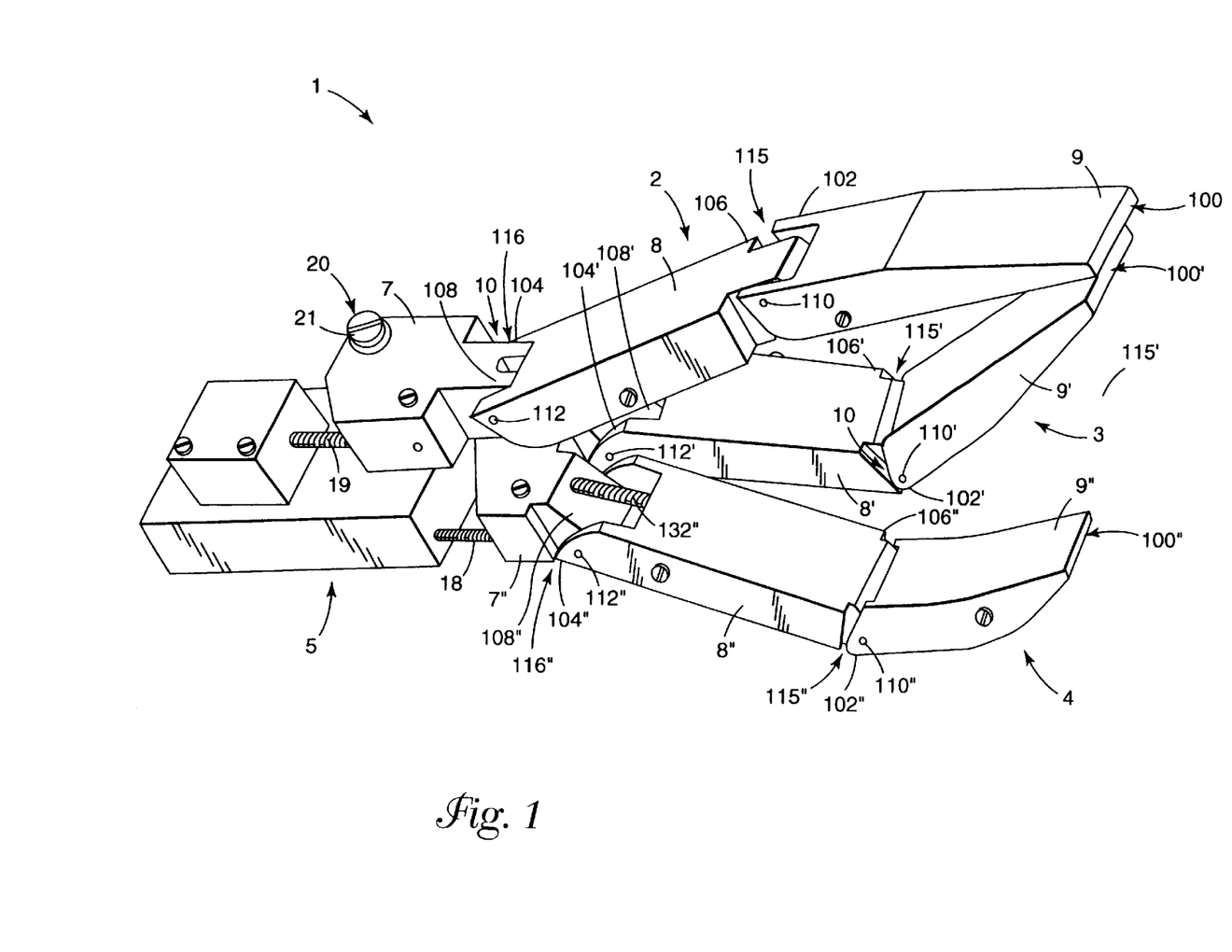
FIG. 1 is a perspective view of one embodiment of a robot hand generally according to the present invention.
Figure 5:
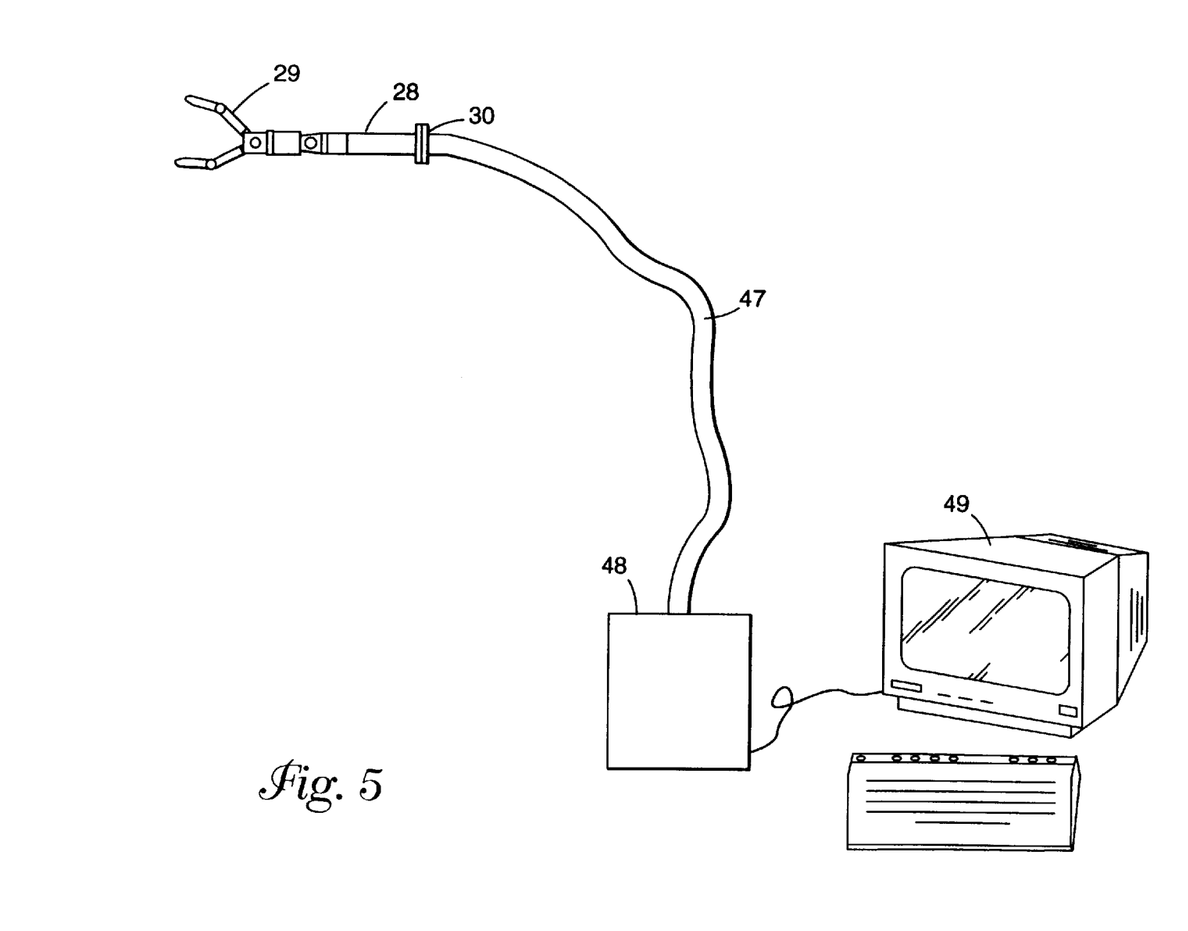
FIG. 5 is a schematic view of a control system in connection with a robot hand.

Referring to the figures, wherein like numbers refer to like parts throughout the several views, FIG. 1 shows a robot hand 1 generally consistent with the principles of the present invention. The robot hand 1 is constructed to mimic movements of a human hand. The robot hand 1 can be operated mechanically by a remote human hand. Alternatively, the robot hand 1 can be operated electrically, receiving input instructions from a data glove or a computer, as generally shown in FIG. 5.

Figure 2:
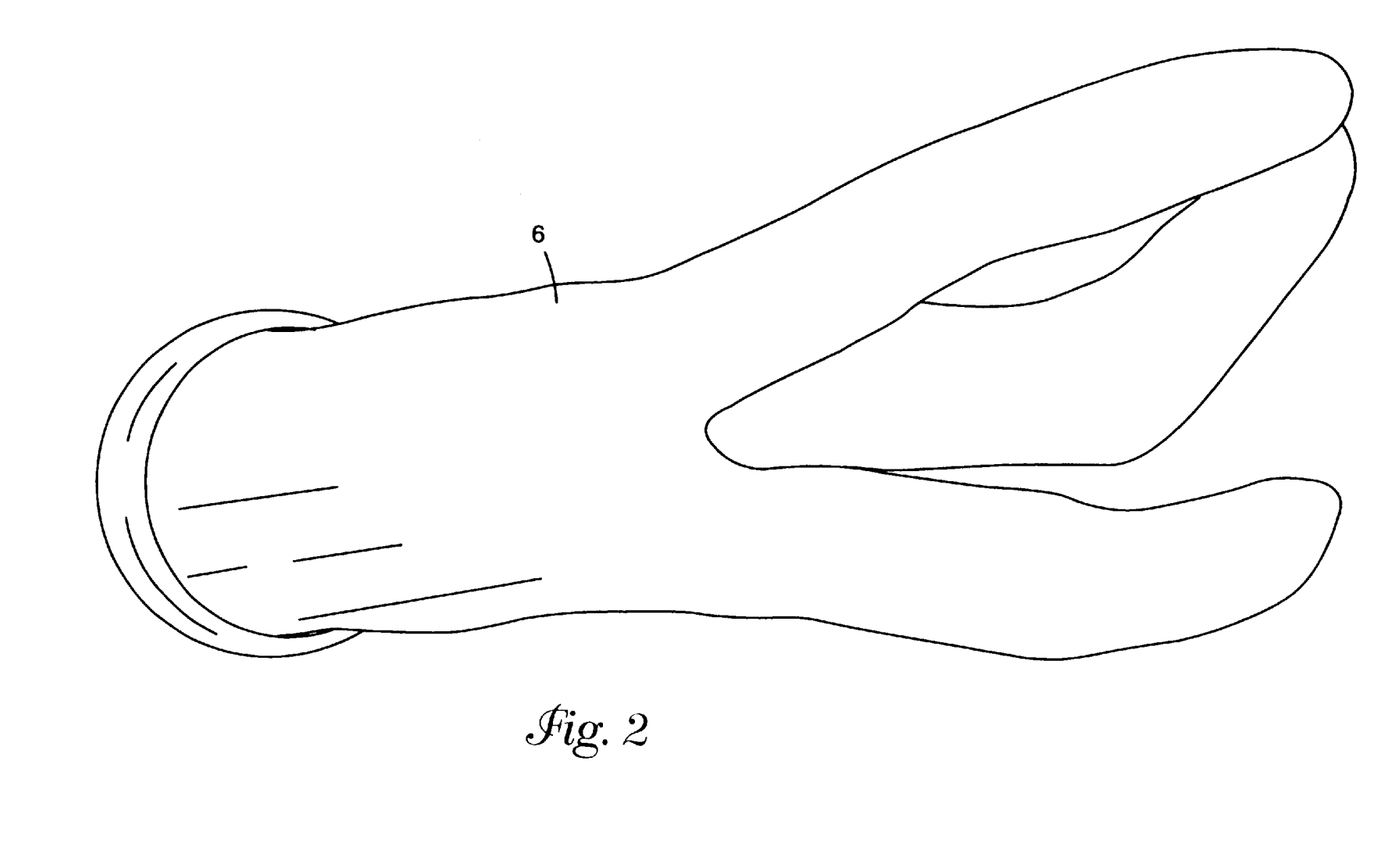
FIG. 2 is a schematic view of one embodiment of a glove for the robot hand.

In FIG. 1, the illustrated robot hand 1 is similar to a human hand in that it has a thumb 2, a first finger 3, a second finger 4, and a hand base 5. The robot hand 1 can be covered by a glove 6 as shown in FIG. 2. As shown in FIG. 1, the thumb 2 includes a base phalanx 7, a middle phalanx 8, and an end phalanx 9. The fingers 3,4 include a base phalanx 7',7", a middle phalanx 8',8", and an end phalanx 9',9", respectively. Each end phalanx 9,9',9" is disposed at a distal end 100, 100', 100" of the thumb 2 or fingers 3,4. Each end phalanx 9,9',9" has a proximal end 102,102',102". Each middle phalanx 8,8', 8" has a proximal end 104,104'104" and a distal end 106,106',106". Each base phalanx 7,7',7" has a distal end 108,108',108". The proximal end 102,102',102" of the end phalanx 9,9',9" is pivotably attached or coupled to the distal end 106,106',106" of the middle phalanx 8,8',8" for rotation around a distal axis 110,110',110". The proximal end 104, 104',104" of the base phalanx 7,7",7" is pivotably attached or coupled to the distal end 108,108',108" of the base phalanx 7, 7', 7"for rotation around a proximal axis 112, 112',112". The distal axis and the proximal axis are substantially parallel when the middle phalanx 108, 108', 108" is substantially linear. Each phalanx is connected to the next phalanx by a joint 10. As shown in FIG. 1, the end phalanx 9,9',9" is coupled to the distal phalanx 8,8',8" by a middle phalanx joint 115, 115', 115"; and the middle phalanx 8,8',8" is coupled to the base phalanx 7,7',7" by a proximal phalanx joint 116, 116', 116". The joint 10 can be any type of suitable connectors, including a coupled hinge, as shown.

FIG. 2 shows the robot hand 1 covered by glove 6, which is made out of an elastic material, such as silicone, latex or any other suitable rubber or elastic material. The glove 6 can serve to protect the mechanics of the robot hand 1. The glove 6 also can provide for repeated sterile use of robot hand 1 and reduce the cleaning necessary after use. In addition, glove 6 can make it easier for the gloved robot hand to move along a lumen or other medical guide, such as a trocar, for insertion of the device into a body. The glove further helps reduce the possibilities of pinching of structures along the path that the robot hand passes. Furthermore, the glove 6 can be disposable after an operation using the robot hand 1, e.g. an endoscopic surgical procedure. It will be appreciated that the robot hand 1 can comprise additional fingers, for example, fingers 4, 5 etc., similar to the fingers 3, 4. It will also be appreciated that the hand glove 6 can be made corresponding to the modified robot hand, e.g. with additional fingers, without departing from the scope and spirit of the present invention.

Figures 3A, 3B:
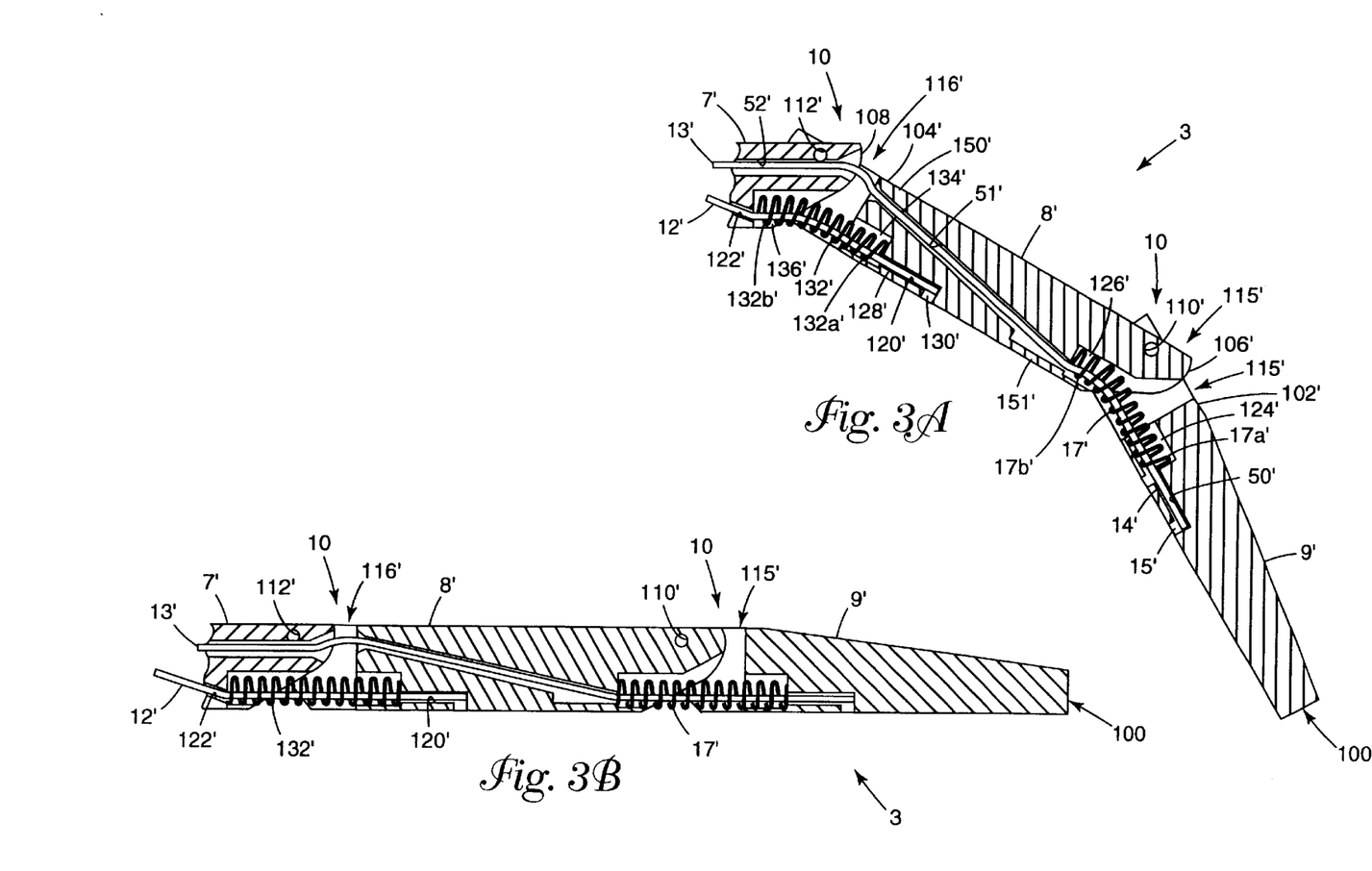
FIG. 3A is a longitudinal, cross-sectional view of a finger of the hand when a portion of the finger is pulled such that the finger is in a bent position.
FIG. 3B is a longitudinal, cross-sectional view of a finger of the hand when the finger is released such that the finger is in a straight position.

In FIGS. 3A and 3B, a longitudinal cross-sectional view of the first finger 3 is shown. The cross-sectional views of FIGS. 3A and 3B could also be representative of finger 4 or thumb 2. As illustrated, middle phalanx joint 115' connects the end phalanx 9' to the middle phalanx 8' so that the end and middle phalanxes 9' and 8' are relatively rotatable around the distal axis 110'. Proximal phalanx joint 116' connects the middle phalanx 8' to the base phalanx 7' so that the middle and base phalanxes 7' and 8' are relatively rotatable around the proximal axis 112'.

The positioning of the phalanxes can be operated by a pulley mechanism utilizing cables. As used herein, a "cable" includes single or multiple stranded wire, plastic, or otherwise suitable material for operating a robot hand as disclosed herein. In the illustrated embodiment, cable 13' extends in a bore 50' of the end phalanx 9', a bore 51' of the middle phalanx 8', and a bore 52' of the base phalanx 7'. The distal end of the cable 13' is connected to the end phalanx 9' at location 14' distal to the proximal end 102' of the end phalanx 9'. The cable 13' can be fastened by a compression screw inserted via hole 15' or other means such as welding, gluing, etc. A spring 17' is disposed around a portion of the cable 13' proximate the middle phalanx joint 115' between the end phalanx 9' and the middle phalanx 8'. The two ends, 17a' and 17b', of the spring 17' are retained in notches 124', 126' of the end phalanx 9' and the middle phalanx 8', respectively. The spring 17', biased against and between the walls of the two notches 124', 126', can be a spiral spring, a flat spring or equivalent structure. The cable 13' is operated to rotate the end phalanx 9', and the middle phalanx 8', relative to one another, which mimics movements of a finger or thumb between the end and middle phalanxes. Accordingly, when the cable 13' is pulled in a direction of the hand base 5 (FIG. 1), the end phalanx 9' rotates around the middle phalanx 8' around the distal axis 110' as shown in FIG. 3A. When the force to cable 13' is released, the spring 17' biases back the end phalanx 9' from the middle phalanx 8' around the distal axis 110' so as to straighten the finger 3 as shown in FIG. 3B.

Another pulley or cable 12' extends in a bore 120' of the middle phalanx 8 and a bore 122' of the base phalanx 7'. The distal end of the cable 12' is connected to the middle phalanx 8' at location 128' distal to the proximal end 104' of the middle phalanx 8'. This connection can be done by fastening using a screw inserted via hole 130' or other means such as welding, gluing, etc. A spring 132' is disposed around a portion of the cable 12' proximate the proximal phalanx joint 116' between the middle phalanx 8' and the base phalanx 7'. The two ends, 132a' and 132b', of the spring 132' are retained in notches 134', 136' of the middle phalanx 8' and the base phalanx 7', respectively. The spring 132', biased against and between the walls of the two notches 134', 136', can be a spiral spring, a flat spring or equivalent structure. The cable 12' is operated to rotate the middle phalanx 8' around the base phalanx 7', which mimics movements of a digit (finger or thumb) between the middle and base phalanxes. Accordingly, when the cable 12' is pulled in a direction of the hand base 5', the middle phalanx 8' moves relative to the base phalanx 7' as shown in FIG. 3A. When the force to cable 12' is released, the spring 132' biases back the middle phalanx 8' from the base phalanx 7' so as to straighten the finger 3 as shown in FIG. 3B.

Finger 4 and thumb 2 have a similar longitudinal cross-sectional view as shown in FIGS. 3A and 3B. As a result, the two cables (12', 13') of each of the fingers 3 and 4 move the middle phalanxes 8',8" against the base phalanxes 7',7" and move the end phalanxes 9',9" against the middle phalanxes 8',8".

As shown in FIG. 1, the fingers 3 and 4 are generally disposed to oppose the thumb 2 such that the movements between the thumb 2 and each of the fingers 3 and 4 allow gripping therebetween. That is, like a human hand, a robot hand according to the invention has an opposable thumb.

Further in FIG. 1, a spring 18 is connected between the base phalanx 7" of finger 4 and hand base 5. The spring 18 is used to move back (adduct) finger 4 with respect to the finger 3. Another spring (not visible) is connected between the base phalanx 7' of finger 3 and the hand base 5. This spring is positioned such that it can move back (adduct) finger 3 with respect to finger 4. Thus, these springs assist in moving the fingers together. A pulley or cable (not visible) runs through spring 18. When pulled towards hand base 5, the cable moves finger 4 away from finger 3 (abduction). A similar cable can move finger 3 away from finger 4 (abduction).

Still referring to FIG. 1, the thumb 2 can pivot around an axis through pivotal connector 20 or similar pivot arrangement, by means of a cable (not visible), and a pullback-spring 19. Pivotal connector 20 can be a screw 21, or other suitable structure. Pivotal connector 20 allows the thumb 2 to move transversely. As a result, the thumb 2 can move to oppose a selected finger, so as to grip between the thumb and the selected individual finger. Thumb 2 can also move with respect to the fingers in a direction determined by the positioning of the proximal and middle phalanx joints. This provides for control of the force of the grip between the thumb and a finger. Accordingly, the robot hand with the thumb and fingers can mimic the movements of a hand with an opposable thumb, e.g. a human hand.

Figure 4A:
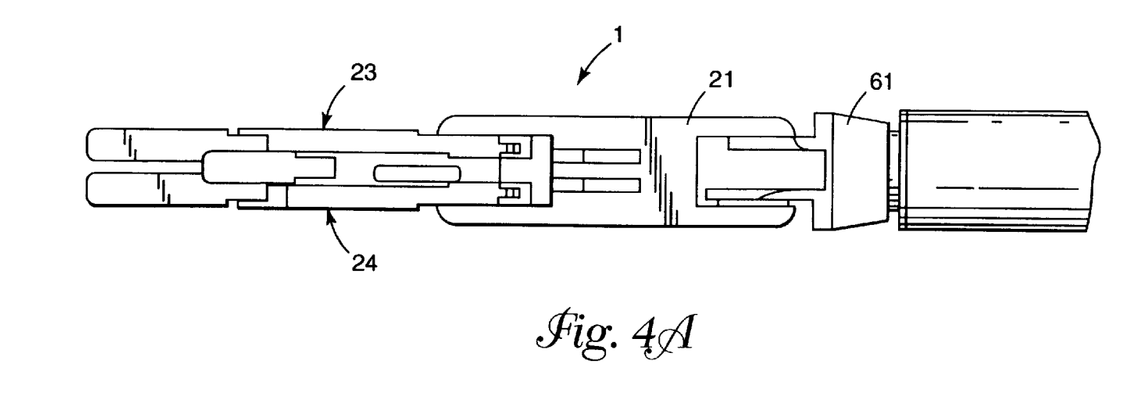
FIG. 4A is a plane top view of another embodiment of a robot hand.
Figure 4B:
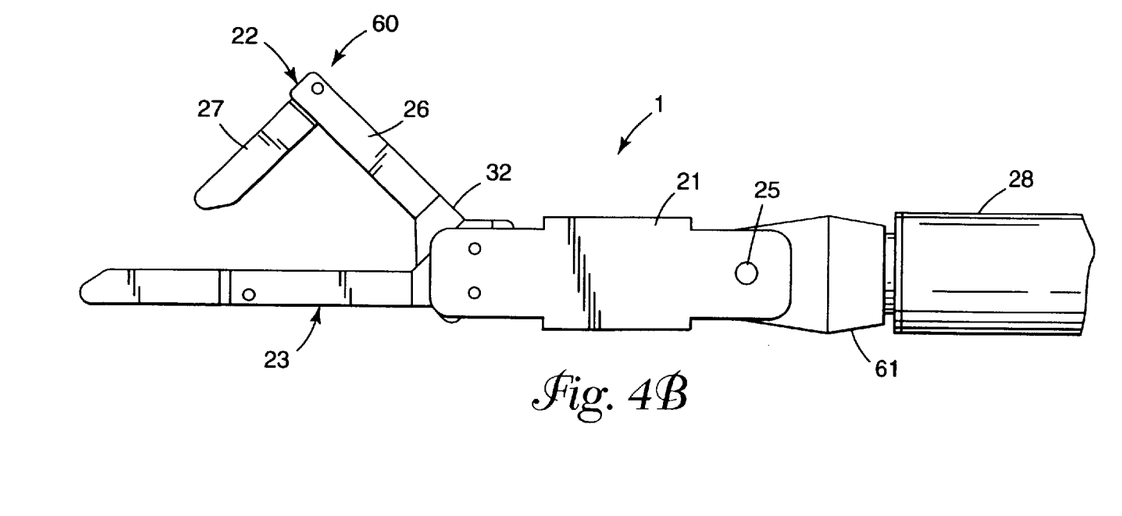
FIG. 4B is an elevational side view of the embodiment of the robot hand of FIG. 4A.

Referring to FIGS. 4A and 4B, a second embodiment of a robot hand 1 is shown. FIG. 4A is a top view of robot hand 1. FIG. 4B is a side view of robot hand 1. The robot hand 1 comprises a hand piece 21 with a thumb 22, a first finger 23, and a second finger 24. According to this embodiment, the robot hand 1 can rotate via cables using a pulley mechanism around a pivot point 25 but may not be able to spread (abduct) fingers 23 and 24. In FIGS. 4A and 4B, the robot hand 1 includes a wrist region 61. The thumb 22 has two phalanxes 26 and 27 which are connected at joint 60. The joint 60, between phalanxes 26 and 27, can be similar to joints 115, 115', 115", 116, 116' or 116" as described for FIG. 1. In FIG. 4A, phalanx 26 is extended relative to hand piece 21 and phalanx 27 is flexed relative to phalanx 26.

It will be appreciated that when the fingers/thumb are generally in their straight positions, the robot hand 1 with a shaft 28 attached to the hand can pass through a medical guide such as a trocar. That is, in one embodiment, the robot hand device is of an appropriate size to pass through a small incision for use in a minimally invasive procedure such as a laparoscopic procedure.

Referring again to FIGS. 3A and 3B, the operation of finger 3 is demonstrated. It will be appreciated that the discussion related to operation and function of finger 3 is applicable to thumb 2, finger 4 and any additional fingers which may be used. The cables 12' and 13' can be pulled either by a remote controller or a local controller. As discussed above, the cable 13' is shown to be located in the finger to pass on the volar aspect 151 ' of the proximal axis 112' through proximal phalanx joint 116' between the base phalanx 7' and the middle phalanx 8', pass into the dorsal aspect 150' of middle phalanx 8' down to the volar aspect 151 ' of the middle phalanx 8' through the spring 17', and is connected to the end phalanx 9' in the hole 15' at 14'. If the cable 13' is pulled, the cable 13' rotates the end phalanx 9' relative to the middle phalanx 8'. If the cable 13' is loosened, the spring 17' biases against the end phalanx 9' which will tend to straighten the finger between the end phalanx 9' and the middle phalanx 8'. The cable 13' does not move the proximal phalanx joint 116', because the cable 13' does not have a spring around it and will cross the joint 116' near the pivot point of proximal axis 112'. FIG. 3B shows the finger 3 in a straight position where the spring 17' straightens the finger.

FIG. 5 shows that the shaft 28 can be disconnected from a flexible transfer unit 47 by a disconnecting unit 30 so that an exemplary robot hand 29 can be disconnected from the system to be sterilized or disposed and/or changed with a new hand. The cables are retained inside a flexible transfer unit 47 and connected to a motor unit 48. Operational motors of motor unit 48 can be controlled by a computer 49.

Figure 6:
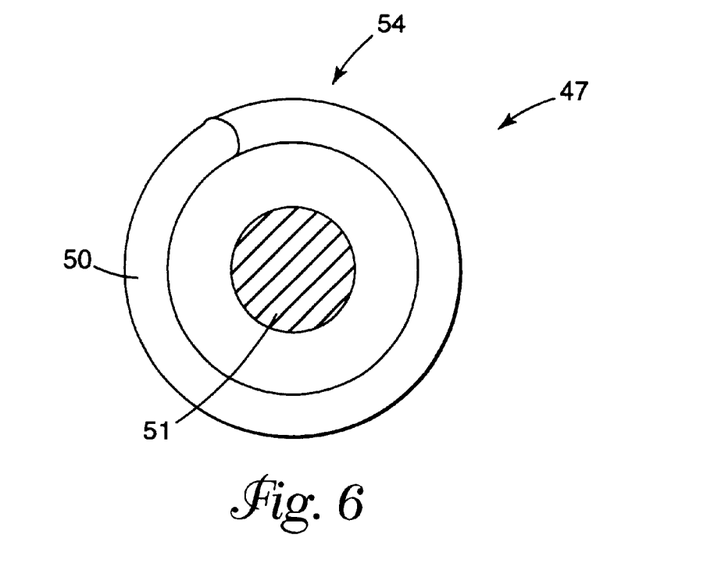
FIG. 6 is a transverse, cross-sectional view of a pulley cable.
Figure 7:
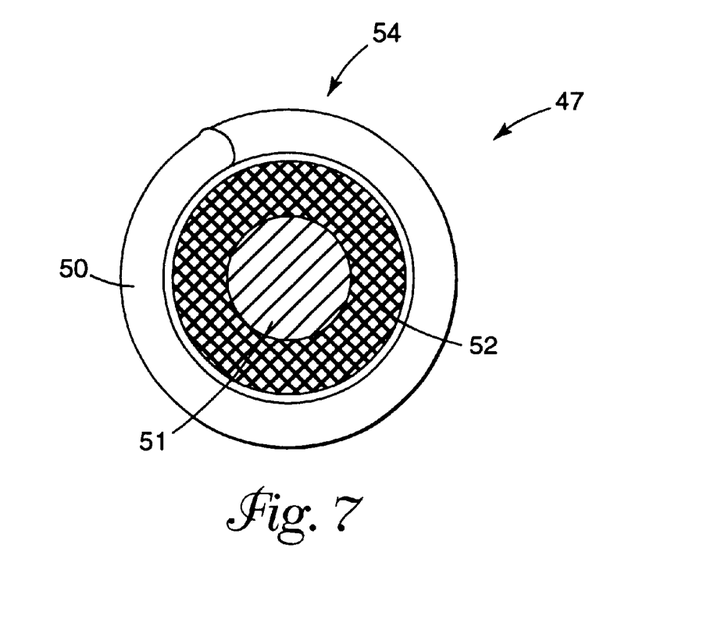
FIG. 7 is a transverse, cross-sectional view of another embodiment of a pulley cable.

FIG. 6 shows a cross-section of flexible transfer unit 47 including a pulley or cable 54 having a core assembly 51 and a sheath 50. FIG. 7 shows the cross-section of another type of flexible transfer unit 47 including a pulley or cable 54 with a core assembly 51, a sheath 50, and a filling 52.

Figure 8:
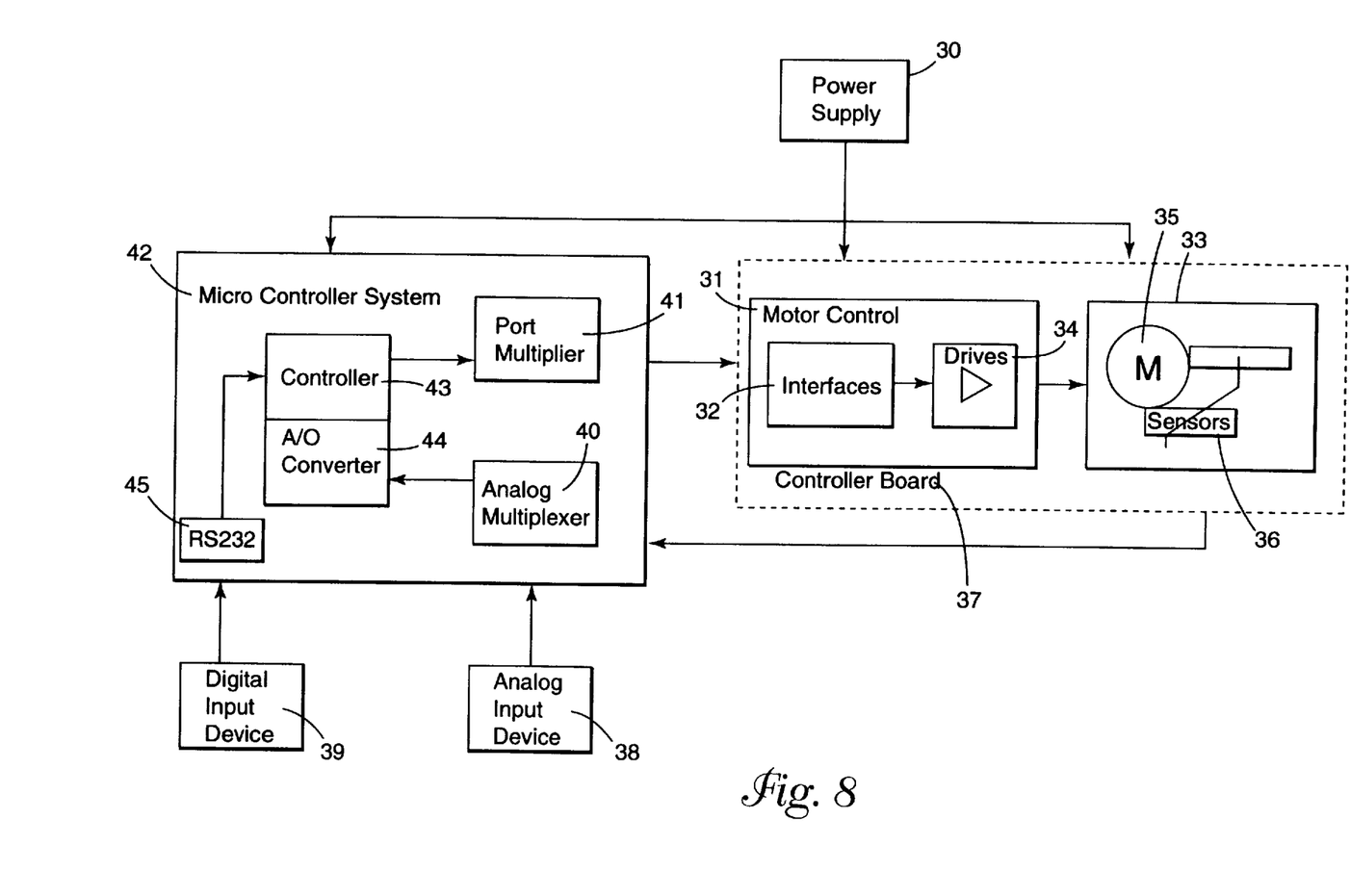
FIG. 8 is a block diagram of a control system of the robot hand.

FIG. 8 illustrates a schematic view of a circuit of a control system for operating a robot hand. In one embodiment, all control functions are operated and controlled by a micro controller system 42. The robot hand can be controlled by a digital input device 39 or an analog input device 38. The analog input device 38 presets nominal values for the movement of the robot hand.

Program and data for a controller 43 are saved in a working memory. An A/D converter 44 together with an analog multiplexer 40 is used for acquisition of measured values for positioning a robot hand. The serial interfaces RS232 (45) are used to control the robot hand from a master system and to connect the digital input device 39.

The controller 43 produces directional signals which are transmitted by a port multiplexer 41 to a motor controller 31 to control motors 35. The motor controller 31 generates special signals for the motors 35 with interfaces 32 and powers the signals with drivers 34. The motors 35 can be linear motors or rotary motors. It will be appreciated that other types of suitable motors can be used.

In one embodiment, the analog multiplexer 40 transmits the signal of position sensors 36 in the robot hand to a channel of the A/D converter 44. A power supply 30 delivers power with a suitable voltage for the motors 35 and for the micro-controller system 42 and port extensions.

One method of operating a robot hand is as follows:
balancing particular channels (e.g. balance of initial and end values) by manual or other means;
calibrating the robot hand automatically;
adjusting all axes to an analog nominal value;
adjusting all axes to an analog nominal value and memorizing values;
reproducing memorized values in form of movements; and
adjusting all axes to a digital nominal value.

It will be appreciated that the thumbs 2, 22 and fingers 3, 4, 23, 24 and other parts of the robot hand are exemplary and can be varied in size, shape, and relative position without departing from the principles of the present invention. It will also be appreciated that the locations and extending directions of the pulleys (or cables), springs, joints, notches, pivotal connections, etc., can be varied according to the principles of the present invention.

In addition, the thumb and fingers of the robot hand can be made of metal, such as stainless steel, or plastic or a combination of plastic and metal. The pulleys (or cables) can be made out of steel wires. It will be appreciated that other suitable materials can be used without departing from the principles of the invention.

Further, in one embodiment, the robot hand is made in a dimension which allows the hand to pass through a 10 mm diameter trocar. It will be appreciated that other dimensions can be used according to the principles of the invention. One of the advantages of having a smaller dimension is that it allows a smaller "human" hand, i.e. a robot hand, to mimic movements of a real human hand in limited space environments.

A device of the invention can be operated using mechanical input information from a human hand or electrical input information from a computer or from a human hand through a glove worn by an operator for detecting finger positions by the operator and operatively connecting the detected position to the device.

As one skilled in the art appreciates that various modifications may be made to the above described embodiment without departing from the spirit and scope of the invention, the invention thus resides in the claims hereafter appended.

What is claimed is:
1. A robot hand comprising:
   a thumb including:
      a thumb base phalanx; a thumb middle phalanx; a thumb distal phalanx;
      a first pivotal thumb joint between the thumb distal phalanx and the thumb middle phalanx;
      a second pivotal thumb joint between the thumb middle phalanx and the thumb base phalanx;
      a first thumb cable passing through the thumb base phalanx and the thumb middle phalanx and attaching to the thumb distal phalanx, and a second thumb cable passing through the thumb base phalanx and attaching to the thumb middle phalanx, the thumb being transversely movable with respect to movement of the thumb phalanxes about the first and second thumb joints; and
   at least two fingers disposed on an opposite side of the thumb, each of the fingers including:
      a finger base phalanx; a finger middle phalanx; a finger distal phalanx;
      a first pivotal finger joint between the finger distal phalanx and the finger middle phalanx; a second pivotal finger joint between the finger middle phalanx and the finger base phalanx;
      a first finger cable passing through the finger base phalanx and the finger middle phalanx and attaching to the finger distal phalanx and a second finger cable passing through the finger base phalanx and attaching to the finger middle phalanx; and
      at least one spiral spring disposed at at least one of the pivotal thumb and finger joints to spring-bias the at least one of the thumb and finger joints in a straight position;
   wherein one of the at least one of the pivotal thumb and finger joints is bent upon exertion of a force on a cable associated with the one of the at least one of the pivotal thumb and finger joints.

2. A robot hand according to claim 1, wherein at least one of the cables is moved by a controller.

3. A robot hand according to claim 2, further comprising a flange, the robot hand being disconnectable by the flange from a controlling system.

4. A robot hand according to claim 1, wherein one of the first thumb cable and the first finger cables passes through the at least one spiral spring.

5. A robot hand according to claim 1, further comprising a disposable glove which houses the thumb and the at least two fingers.

6. A robot hand according to claim 1, wherein when the thumb and at leat two fingers are in a substantially linear position, the hand can be passed through a medical trocar.

7. A robot hand according to claim 1, wherein the at least two fingers can abduct and adduct relative to each other.

8. A robot hand according to claim 1 wherein the thumb is moveable such as to oppose a selected one of the at least tow fingers and grip between the selected one of at least two fingers.

9. A robot hand according to claim 1 wherein the first thumb cable attaches to a proximal end of the distal thumb phalanx.

10. A robot hand according to claim 1 wherein the first thumb cable passes through the thumb base phalanx on a volar aspect of a pivot axis at the second thumb joint.

11. A robot hand according to claim 1, wherein the second pivotal finger joint defines a first axis of rotation at a pivot, the finger base phalanx defines a finger base phalanx longitudinal axis between a distal end of the finger base phalanx and a proximal end of the finger base phalanx, and the at least one spring includes a first spring disposed relative to the pivot in a direction substantially perpendicular to both the finger base phalanx longitudinal axis and the first rotation axis.

12. A robot hand according to claim 11, wherein the first spring is a coil spring and has a longitudinal spring axis substantially parallel to the finger base phalanx longitudinal axis when the first spring is in a relaxed position, and the second finger cable passes through the coil spring.

13. A robot hand according to claim 11, wherein the first finger cable passes between the first spring and the pivot to the finger middle phalanx, closer to the pivot than to the first spring.

14. A robot hand according to claim 1, further comprising a hand base, the thumb base phalanx and the finger base phalanx each being attached to the hand base, wherein, when the thumb and the at least two fingers are in a relaxed position without significant tension on the thumb cables and the finger cables, the at least two fingers and thumb lie substantially parallel to one another, pointing in a distal direction from the hand base to pass through a trocar.

15. A robot hand comprising:
 a hand base;
 at least two fingers, each of the fingers including:
  a first finger phalanx attached to the hand base and a second finger phalanx;
  a first pivotal finger joint connecting the first finger phalanx and the second finger phalanx;
  a first finger cable passing through the first finger phalanx and attaching to the second finger phalanx; and
  a finger joint spring disposed between the first and second finger phalanges, at the first pivotal finger joint, to spring-bias the first finger joint so that the second finger phalanx is substantially parallel to the first finger phalanx,
  wherein the first finger joint is bent upon exertion of a force on the first finger cable; and
 a thumb opposing the first two fingers, the thumb including:
  a first thumb phalanx attached to the hand base and a second thumb phalanx;
  a first pivotal thumb joint connecting the first thumb phalanx and the second thumb phalanx;
  a first thumb cable passing through the first thumb phalanx and attaching to the second thumb phalanx;
  a spring disposed between the first and second thumb phalanges, at the first pivotal thumb joint, to spring-bias the first thumb joint so that the second thumb phalanx is substantially parallel to the first thumb phalanx,
  wherein the first pivotal thumb joint is bent upon exertion of a force on the first thumb cable, and
 a third phalanx pivotally attached to one of the second thumb phalanx and the second finger phalanges, a second cable passing through the one of the second thumb phalanx and second finger phalanges and attaching to the third phalanx, a third phalanx spring being positioned between the third phalanx and the one of the second thumb phalanx and second finger phalanges to spring-bias the third phalanx to be substantially parallel to the one of the second thumb phalanx and second finger phalanges when there is no spring-bending tension on the second cable.

16. A robot hand as recited in claim 15 wherein, in at least one of the fingers, the first finger pivotal joint defines a first axis of rotation and the first finger phalanx is pivotally attached to the hand base to pivot about an axis substantially perpendicular to the first axis of rotation.

17. A robot hand as recited in claim 15, wherein, in at least one of the fingers, the first pivotal finger joint defines a first axis of rotation at a pivot and the first finger phalanx defines first finger phalanx longitudinal axis between a distal end of the first finger phalanx and a proximal end of the first finger phalanx, and the spring is disposed relative to the pivot in a direction substantially perpendicular to both the first axis of rotation and the first finger phalanx longitudinal axis.

18. A robot hand according to claim 17, wherein the spring is a coil spring and has a longitudinal spring axis substantially parallel to the first finger phalanx longitudinal axis when the coil spring is in a relaxed position, and the first finger cable passes through the coil spring between the first and second finger phalanges.

19. A robot hand comprising:
 a thumb including:
  a thumb base phalanx; a thumb middle phalanx; a thumb distal phalanx;
  a first pivotal thumb joint between the thumb distal phalanx and the thumb middle phalanx;
  a second pivotal thumb joint between the thumb middle phalanx and the thumb base phalanx;
  a first thumb cable passing through the thumb base phalanx and the thumb middle phalanx and attaching to the thumb distal phalanx, and a second thumb cable passing through the thumb base phalanx and attaching to the thumb middle phalanx, the thumb being transversely movable with respect to movement of the thumb phalanxes about the first and second thumb joints; and
 at least two fingers disposed on an opposite side of the thumb, each of the fingers including:
  a finger base phalanx; a finger middle phalanx; a finger distal phalanx;
  a first pivotal finger joint between the finger distal phalanx and the finger middle phalanx; a second pivotal finger joint between the finger middle phalanx and the finger base phalanx;
  a first finger cable passing through the finger base phalanx and the finger middle phalanx and attaching to the finger distal phalanx and a second finger cable passing through the finger base phalanx and attaching to the finger middle phalanx; and
  at least one spring disposed at at least one of the pivotal thumb and finger joints to spring-bias the at least one of the thumb and finger joints in a straight position,
 wherein one of the at least one of the pivotal thumb and finger joints is bent upon exertion of a force on a cable associated with the one of the at least one of the pivotal thumb and finger joints, and the second pivotal finger joint defines a first axis of rotation at a pivot, the finger base phalanx defines a finger base phalanx longitudinal axis between a distal end of the finger base phalanx and a proximal end of the finger base phalanx, and the at least one spring includes a first spring disposed relative to the pivot in a direction substantially perpendicular to both the finger base phalanx longitudinal axis and the first rotation axis.

20. A robot hand according to claim 19, wherein at least one of the cables is moved by a controller.

21. A robot hand according to claim 20, further comprising a flange, the robot hand being disconnectable by the flange from a controlling system.

22. A robot hand according to claim 19, wherein one of the first thumb cable and the first finger cables passes through the at least one spring.

23. A robot hand according to claim 19, further comprising a disposable glove housing the thumb and the at least two fingers.

24. A robot hand according to claim 19, wherein the at least two fingers can abduct and adduct relative to each other.

25. A robot hand according to claim 19, wherein the first spring is a coil spring and has a longitudinal spring axis substantially parallel to the finger base phalanx longitudinal axis when the first spring is in a relaxed position, and the second finger cable passes through the coil spring.

26. A robot hand according to claim 19, wherein the first finger cable passes between the first spring and the pivot to the finger middle phalanx, closer to the pivot than to the first spring.

27. A robot hand according to claim 19, further comprising a hand base, the thumb base phalanx and the finger base phalanx each being attached to the hand base, wherein, when the thumb and the at least two fingers are in a relaxed position without significant tension on the thumb cables and the finger cables, the at least two fingers and thumb lie substantially parallel to one another, pointing in a distal direction from the hand base to pass through a trocar.

28. A robot hand comprising:
   a thumb including:
      a thumb base phalanx; a thumb middle phalanx; a thumb distal phalanx;
      a first pivotal thumb joint between the thumb distal phalanx and the thumb middle phalanx;
      a second pivotal thumb joint between the thumb middle phalanx and the thumb base phalanx;
      a first thumb cable passing through the thumb base phalanx and the thumb middle phalanx and attaching to the thumb distal phalanx, and a second thumb cable passing through the thumb base phalanx and attaching to the thumb middle phalanx, the thumb being transversely movable with respect to movement of the thumb phalanxes about the first and second thumb joints; and
   at least two fingers disposed on an opposite side of the thumb, each of the fingers including:
      a finger base phalanx; a finger middle phalanx; a finger distal phalanx;
      a first pivotal finger joint between the finger distal phalanx and the finger middle phalanx; a second pivotal finger joint between the finger middle phalanx and the finger base phalanx;
      a first finger cable passing through the finger base phalanx and the finger middle phalanx and attaching to the finger distal phalanx and a second finger cable passing through the finger base phalanx and attaching to the finger middle phalanx; and
      a first spring disposed at one of the pivotal thumb and finger joints to spring-bias the one of the thumb and finger joints in a straight position,
   wherein the one of the pivotal thumb and finger joints is bent upon exertion of a force on a cable associated with the one of the at least one of the pivotal thumb and finger joints, and the cable associated with the one of the pivotal thumb and finger joints passes between the first spring and a pivot of the one of the pivotal thumb and finger joints, closer to the pivot than to the first spring.

29. A robot hand according to claim 28, wherein at least one of the cables is moved by a controller.

30. A robot hand according to claim 28, further comprising a flange, the robot hand being disconnectable by the flange from a controlling system.

31. A robot hand according to claim 28, wherein one of the first thumb cable and the first finger cables passes through the first spring.

32. A robot hand according to claim 28, further comprising a disposable glove housing the thumb and the at least two fingers.

33. A robot hand according to claim 28, wherein the at least two fingers can abduct and adduct relative to each other.

34. A robot hand according to claim 28, wherein the second pivotal finger joint defines a first axis of rotation at a pivot, the finger base phalanx defines a finger base phalanx longitudinal axis between a distal end of the finger base phalanx and a proximal end of the finger base phalanx, and the first spring is disposed relative to the pivot in a direction substantially perpendicular to both the finger base phalanx longitudinal axis and the first rotation axis.

35. A robot hand according to claim 34, wherein the first spring is a coil spring and has a longitudinal spring axis substantially parallel to the finger base phalanx longitudinal axis when the first spring is in a relaxed position, and the second finger cable passes through the coil spring.

36. A robot hand according to claim 28, further comprising a hand base, the thumb base phalanx and the finger base phalanx each being attached to the hand base, wherein, when the thumb and the at least two fingers are in a relaxed position without significant tension on the thumb cables and the finger cables, the at least two fingers and thumb lie substantially parallel to one another, pointing in a distal direction from the hand base to pass through a trocar.

37. A robot hand comprising:
   a hand base;
   at least two fingers, each of the fingers including:
      a first finger phalanx attached to the hand base and a second finger phalanx;
      a first pivotal finger joint connecting the first finger phalanx and the second finger phalanx;
      a first finger cable passing through the first finger phalanx and attaching to the second finger phalanx; and
      a finger joint spring disposed between the first and second finger phalanges, at the first pivotal finger joint, to spring-bias the first finger joint so that the second finger phalanx is substantially parallel to the first finger phalanx, the first being bent upon exertion of a force on the first finger cable; and
   a thumb opposing the first two fingers, the thumb including:
      a first thumb phalanx attached to the hand base and a second thumb phalanx;
      a first pivotal thumb joint connecting the first thumb phalanx and the second thumb phalanx;
      a first thumb cable passing through the first thumb phalanx and attaching to the second thumb phalanx;
      a spring disposed between the first and second thumb phalanges, at the first pivotal thumb joint, to spring-bias the first thumb joint so that the second thumb phalanx is substantially parallel to the first thumb phalanx, the first pivotal thumb joint being bent upon exertion of a force on the first thumb cable
   wherein, in at least one of the fingers, the first pivotal finger joint defines a first axis of rotation at a pivot and the first finger phalanx defines first finger phalanx longitudinal axis between a distal end of the first finger phalanx and a proximal end of the first finger phalanx, and the spring is disposed relative to the pivot in a direction substantially perpendicular to both the first axis of rotation and the first finger phalanx longitudinal axis.

38. A robot hand as recited in claim 37, wherein, in at least one of the fingers, the first finger pivotal joint defines a first axis of rotation and the first finger phalanx is pivotally attached to the hand base to pivot about an axis substantially perpendicular to the first axis of rotation.

39. A robot hand as recited in claim 37, wherein the spring is a coil spring and has a longitudinal spring axis substantially parallel to the first finger phalanx longitudinal axis when the coil spring is in a relaxed position, and the first finger cable passes through the coil spring between the first and second finger phalanges.

40. A robot hand as recited in claim 37, further comprising a third phalanx pivotally attached to one of the second thumb phalanx and the second finger phalanges, a second cable passing through the one of the second thumb phalanx and second finger phalanges and attaching to the third phalanx, a third phalanx spring being positioned between the third phalanx and the one of the second thumb phalanx and second finger phalanges to spring-bias the third phalanx to be substantially parallel to the one of the second thumb phalanx and second finger phalanges when there is no significant tension on the second cable.

* * * * *